(12) United States Patent
McCanna et al.

(10) Patent No.: US 12,605,111 B2
(45) Date of Patent: Apr. 21, 2026

(54) PHYSIOLOGICAL SENSOR PATCH FOR MAKING COMPLEX MEASUREMENTS OF BIOIMPEDANCE

(71) Applicants: Baxter International Inc., Deerfield, IL (US); Baxter Healthcare SA, Glattpark (CH)

(72) Inventors: James Patrick McCanna, San Diego, CA (US); Marshal Singh Dhillon, San Diego, CA (US); Justin Grant Buckingham, Oceanside, CA (US); Matthew John Banet, San Diego, CA (US); Erik Edwin Tang, San Diego, CA (US)

(73) Assignees: BAXTER INTERNATIONAL INC., Deerfield, IL (US); BAXTER HEALTHCARE SA, Glattpark (CH)

( * ) Notice: Subject to any disclaimer, the term of this patent is extended or adjusted under 35 U.S.C. 154(b) by 417 days.

(21) Appl. No.: 18/087,222

(22) Filed: Dec. 22, 2022

(65) Prior Publication Data

US 2023/0200729 A1 Jun. 29, 2023

Related U.S. Application Data

(60) Provisional application No. 63/293,338, filed on Dec. 23, 2021.

(51) Int. Cl.
| | |
|---|---|
| *A61B 5/00* | (2006.01) |
| *A61B 5/0205* | (2006.01) |
| *A61B 5/0537* | (2021.01) |

(52) U.S. Cl.
CPC .......... *A61B 5/4878* (2013.01); *A61B 5/0059* (2013.01); *A61B 5/0205* (2013.01);
(Continued)

(58) Field of Classification Search
None
See application file for complete search history.

(56) References Cited

U.S. PATENT DOCUMENTS

| | | | | | |
|---|---|---|---|---|---|
| 5,353,802 A | * | 10/1994 | Ollmar | ................ | A61B 5/0531 |
| | | | | | 600/547 |
| 5,978,693 A | * | 11/1999 | Hamilton | ............... | A61B 5/259 |
| | | | | | 600/394 |

(Continued)

FOREIGN PATENT DOCUMENTS

| | | |
|---|---|---|
| EP | 2 194 864 A1 | 6/2010 |
| EP | 3 692 908 A1 | 8/2020 |

(Continued)

OTHER PUBLICATIONS

Clarivate Analytics, Translation of WO 2007028570 A2 (Year: 2025).*

(Continued)

*Primary Examiner* — Carl H Layno
*Assistant Examiner* — Manolis Pahakis
(74) *Attorney, Agent, or Firm* — K&L Gates LLP

(57) ABSTRACT

The invention provides a system for characterizing a patient including a substrate, a first electrode, a second electrode, and an electrical system. The electrical system is connected to the substrate and worn entirely on the patient's body. The electrical system in electrical contact with both the first and second electrodes and configured to inject an alternating electrical current through the first electrode and into the region of tissue. The electrical system is configured to measure a first electrical signal from the region of tissue through the second electrode. The electrical system is configured to measure a second electrical signal from the region of tissue. The first electrical signal or a signal determined therefrom indicates a resistance of the region of tissue and (Continued)

the second electrical signal or a signal determined therefrom indicates a reactance of the region of tissue.

18 Claims, 9 Drawing Sheets

(52) U.S. Cl.
CPC .... *A61B 5/0537* (2013.01); *A61B 2562/0261* (2013.01); *A61B 2562/046* (2013.01)

(56) References Cited

U.S. PATENT DOCUMENTS

| | | | | |
|---|---|---|---|---|
| 6,756,793 B2 * | 6/2004 | Hirono | | G01R 27/2605 |
| | | | | 73/335.04 |
| 8,374,688 B2 | 2/2013 | Libbus et al. | | |
| 9,955,916 B2 * | 5/2018 | Bonomi | | A61B 5/086 |
| 11,154,246 B2 | 10/2021 | Inan et al. | | |
| 11,559,220 B2 | 1/2023 | Ha et al. | | |
| 2004/0147819 A1 * | 7/2004 | Caduff | | A61B 5/14532 |
| | | | | 600/316 |
| 2009/0326346 A1 * | 12/2009 | Kracker | | A61B 5/6846 |
| | | | | 600/323 |
| 2012/0150011 A1 * | 6/2012 | Besio | | A61N 1/0408 |
| | | | | 600/372 |
| 2015/0374256 A1 | 12/2015 | Skrabal | | |
| 2016/0310034 A1 * | 10/2016 | Tonar | | A61B 5/742 |
| 2016/0331314 A1 * | 11/2016 | Bhansali | | A61B 5/4878 |
| 2017/0042448 A1 * | 2/2017 | Dovancescu | | A61B 5/0537 |
| 2017/0258995 A1 * | 9/2017 | Hyde | | A61M 35/10 |
| 2018/0289313 A1 * | 10/2018 | Inan | | A61B 5/0537 |
| 2019/0192066 A1 * | 6/2019 | Schoess | | A61B 5/6813 |
| 2019/0200933 A1 | 7/2019 | Yi et al. | | |
| 2020/0352510 A1 * | 11/2020 | Dhillon | | A61B 5/6823 |
| 2021/0145303 A1 | 5/2021 | Moon | | |
| 2021/0228134 A1 * | 7/2021 | Trapero Martin | | G16H 20/60 |
| 2021/0228153 A1 * | 7/2021 | DeCerce | | G01L 5/161 |

FOREIGN PATENT DOCUMENTS

| | | | | | |
|---|---|---|---|---|---|
| WO | WO-9300038 A1 * | 1/1993 | | | A61B 5/0536 |
| WO | WO-2007028570 A2 * | 3/2007 | | | A61B 5/4869 |
| WO | 2017/223552 A1 | 12/2017 | | | |
| WO | 2020/227641 A1 | 11/2020 | | | |

OTHER PUBLICATIONS

PCT/US2022/053867 International Search Report and Written Opinion.

* cited by examiner

IMPEDANCE

OPTICAL

Tissue Impedance – Insulating Fluid Response

Tissue Impedance – Conductive Fluid Response $\Delta T = RS2$

ECG

PCG $\Delta T = RB$

ECG

IPG – AC
(derivative)

$\Delta A = (dZ/dt)_{max}$

IPG – AC
(derivative)

$\Delta T = PAT$

ECG

PPG $\Delta T = RC$

ECG

IPG – AC
(derivative)

$\Delta A = Z_0$

IPG – DC

0

INTs    AMPs

PHYSIOLOGICAL SENSOR PATCH FOR MAKING COMPLEX MEASUREMENTS OF BIOIMPEDANCE

PRIORITY CLAIM AND CROSS-REFERENCE TO RELATED APPLICATIONS

This application claims priority to and the benefit of U.S. Provisional Patent App. No. 63/293,338 filed Dec. 23, 2021, titled PHYSIOLOGICAL SENSOR PATCH FOR MAKING COMPLEX MEASUREMENTS OF BIOIMPEDANCE, the entire contents of which are incorporated by reference herein in their entirety and relied upon.

FIELD OF THE INVENTION

The invention described herein relates to systems for monitoring patients, in both hospital and home environments.

BACKGROUND

Measurement of various patient physiological parameters is of critical importance, for example, in the hospital environment. Current systems typically measure a variety of parameters, including electrocardiogram (ECG), pulse oximetry (SPO$_2$), bioimpedance, and the like. Often, these parameters do not paint the full picture of a patient's status, including overall health trends. Accordingly, improved systems and devices for patient monitoring are therefore needed.

SUMMARY OF THE INVENTION

Given the above, in one aspect, the invention provides a system for monitoring a patient, which involves a number of advanced physiological measurements including, but not limited to, multi-frequency measurements of bioimpedance and/or bioreactance to determine capacitance of underlying tissue and near-infrared spectroscopy (NIRS) measurements.

In a first aspect of the present disclosure, a system for characterizing a patient includes a substrate, a first electrode, a second electrode, and an electrical system. The substrate is configured to be worn on a region of tissue of the patient. The first electrode and the second electrode are both connected to the substrate and attached to the patient above the region of tissue. The electrical system is connected to the substrate and worn entirely on the patient's body. The electrical system is in electrical contact with both the first and second electrodes. The electrical system is configured to: (1) inject an alternating electrical current through the first electrode and into the region of tissue, (2) measure a first electrical signal from the region of tissue through the second electrode, and (3) using both the first and second electrodes measure a second electrical signal from the region of tissue. The first electrical signal or a signal determined therefrom indicates a resistance of the region of tissue and the second electrical signal or a signal determined therefrom indicates a reactance of the region of tissue.

In a second aspect of the present disclosure, which may be combined with any other aspect listed herein unless specified otherwise, the region of tissue is a chest of the patient.

In a third aspect of the present disclosure, which may be combined with any other aspect listed herein unless specified otherwise, the resistance and the reactance are used to determine a bioimpedance measurement.

In a fourth aspect of the present disclosure, which may be combined with any other aspect listed herein unless specified otherwise, the bioimpedance measurement is a complex bioimpedance measurement that includes a real component and an imaginary component.

In a fifth aspect of the present disclosure, which may be combined with any other aspect listed herein unless specified otherwise, the real component is associated with the resistance and the imaginary component is associated with the reactance.

In a sixth aspect of the present disclosure, which may be combined with any other aspect listed herein unless specified otherwise, the system further includes a plurality of strain gauges, configured to measure swelling on the region of tissue.

In a seventh aspect of the present disclosure, which may be combined with any other aspect listed herein unless specified otherwise, the plurality of strain gauges includes four strain gauges.

In an eighth aspect of the present disclosure, which may be combined with any other aspect listed herein unless specified otherwise, the four strain gauges are disposed concentrically around a center point of the region of tissue of the patient.

In a ninth aspect of the present disclosure, which may be combined with any other aspect listed herein unless specified otherwise, the system further includes an optical system, configured to measure swelling on the region of tissue.

In a tenth aspect of the present disclosure, which may be combined with any other aspect listed herein unless specified otherwise, a system for characterizing a patient includes a substrate, a first electrode, a second electrode, and an electrical system. The substrate is configured to be worn on a region of tissue of the patient. The first electrode and the second electrode are both connected to the substrate and attached to the patient above the region of tissue. The electrical system is connected to the substrate and worn entirely on the patient's body. The electrical system is in electrical contact with both the first and second electrodes. The electrical system is configured to (1) inject an alternating electrical current at a plurality of different frequencies through the first electrode and into the region of tissue, and (2) measure a set of electrical signals from the region of tissue through the second electrode, with each electrical signal in the set measured after injecting the alternating electrical current at a unique frequency into the region of tissue. The system further includes a processor in communication with the electrical system configured to receive the set of electrical signals and process them or signals determined therefrom to determine a property corresponding to the region of tissue.

In an eleventh aspect of the present disclosure, which may be combined with any other aspect listed herein unless specified otherwise, the region of tissue is a chest of the patient.

In a twelfth aspect of the present disclosure, which may be combined with any other aspect listed herein unless specified otherwise, the property is a bioimpedance measurement.

In a thirteenth aspect of the present disclosure, which may be combined with any other aspect listed herein unless specified otherwise, a resistance and a reactance are used to determine the bioimpedance measurement.

In a fourteenth aspect of the present disclosure, which may be combined with any other aspect listed herein unless specified otherwise, the bioimpedance measurement is a complex bioimpedance measurement that includes a real component and an imaginary component.

In a fifteenth aspect of the present disclosure, which may be combined with any other aspect listed herein unless specified otherwise, the real component is associated with the resistance and the imaginary component is associated with the reactance.

In a sixteenth aspect of the present disclosure, which may be combined with any other aspect listed herein unless specified otherwise, the system further includes a plurality of strain gauges, configured to measure swelling on the region of tissue.

In a seventeenth aspect of the present disclosure, which may be combined with any other aspect listed herein unless specified otherwise, the plurality of strain gauges includes four strain gauges.

In an eighteenth aspect of the present disclosure, which may be combined with any other aspect listed herein unless specified otherwise, the four strain gauges are disposed concentrically around a center point of the region of tissue of the patient.

In a nineteenth aspect of the present disclosure, which may be combined with any other aspect listed herein unless specified otherwise, the system further includes an optical system, configured to measure swelling on the region of tissue.

In a twentieth aspect of the present disclosure, which may be combined with any other aspect listed herein unless specified otherwise, swelling is measured via time-dependent visual information captured by the optical system.

Additional features and advantages of the disclosed devices, systems, and methods are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein. Moreover, it should be noted that the language used in the specification has been principally selected for readability and instructional purposes, and not to limit the scope of the inventive subject matter.

DETAILED DESCRIPTION

Although the following text sets forth a detailed description of numerous different embodiments, the legal scope of the invention described herein is defined by the words of the claims set forth at the end of this patent. The detailed description is to be construed as exemplary only; it does not describe every possible embodiment, as this would be impractical, if not impossible. One ordinary skill in the art could implement numerous alternate embodiments, which would still fall within the scope of the claims.

1. System Overview

Figure 1:
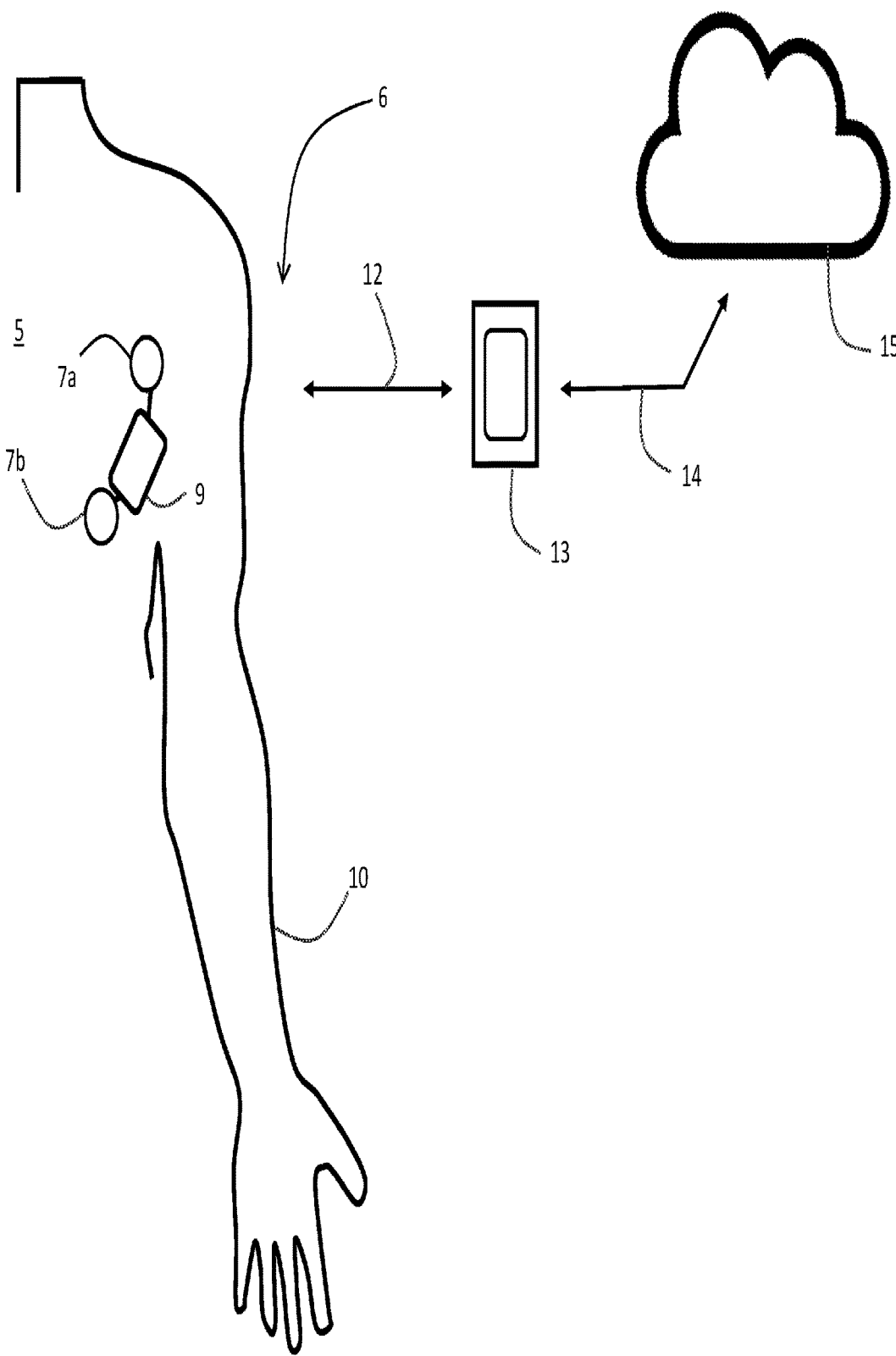
FIG. 1 is a schematic drawing of the system according to the invention featuring a sensor attached to a patient that sends information through a mobile device to a cloud-based system.

Referring to FIG. 1, to monitor a patient at the patient's chest 5, the invention provides a system 6 featuring a pair of body-worn electrode patches 7a, 7b that adhere to the region of interest and connect to a chest-worn component 9.

The chest-worn component 9 encloses a printed circuit board, which features circuitry for making impedance and strain measurements. For the impedance measurement, each body-worn electrode patch 7a, 7b includes a current-injecting electrode and a sensing electrode. Both electrodes typically feature a hydrogel pad that sticks to the patient and conducts current from the current-injecting electrode into the patient and bio-electric signals from the patient. During a measurement, the current-injecting electrode typically injects high-frequency (e.g., 100 kHz), low-amperage (e.g., mean amplitude of 4 mA) current into the portion of the patient; the current and amount of underlying fluid impacts the bio-electric signals sensed by the sensing electrode. The body-worn electrode patches 7a, 7b are typically separated by a few centimeters on the patient. The chest-worn component 9 may include an electrical conductor, such as a strain gauge. Typically, the electrical conductor features a coiled metal strand with an electrical resistance that increases as it is stretched. Alternatively, the conductor may be separated into two unique conductors that sandwich an insulating material on opposing sides, thus effectively forming a variable capacitor. Here, as a cable stretches, the internal conductors on the opposing surface are drawn closer together, thus decreasing the inherent capacitance of the system. In related embodiments, the cable can also include a piezoelectric material that generates a voltage that varies with the amount that it is stretched. In these cases, changes in the electrical properties of the cable-either resistance, capacitance, or voltage—can be easily detected using circuitry within the printed circuit board. Typically, this is done by including a resistor of known resistance in-line with the variable in-cable resistor or a capacitor of known capacitance in-line with the variable in-cable capacitor and then monitoring a voltage drop across the different circuit elements. An internal analog-to-digital converter digitizes the voltage drop. It converts it into a digital DC signal, which can then be processed with an algorithm described below. Similarly, the analog-to-digital converter can measure voltages generated by the piezoelectric material, which indicates the degree of stretching. Algorithms for processing these signals are encoded on a microprocessor on the printed circuit board within the chest-worn component 9 and typically feature a series of processing steps.

A wireless transceiver within the chest-worn component 9, e.g., a Bluetooth® or Wi-Fi transmitter, sends a digitized version of the parameter to a matched transceiver the patient's mobile phone 13 or a clinician's device, as indicated by the arrow 12. The mobile phone 13 then forwards the digitized version of the parameter to a cloud-based system 15, as indicated by the arrow 14. Typically, the cloud-based system 15 renders the parameter for both patients and clinicians or forwards the parameter (e.g., through a web services interface) to a third-party software application, such as a mobile application.

Figure 2A:
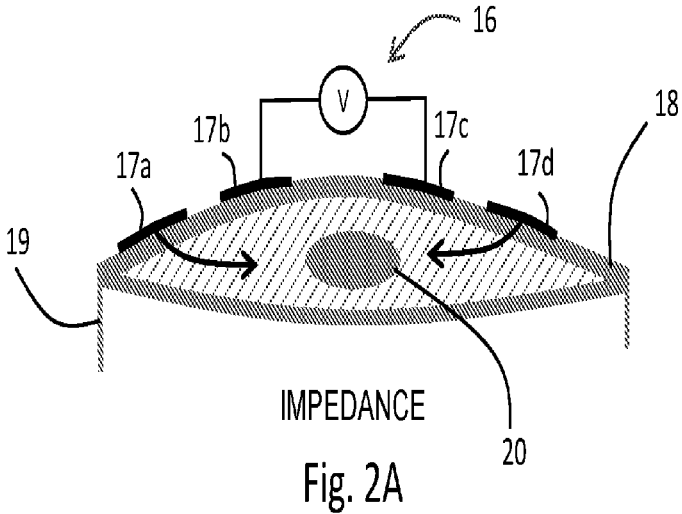
FIGS. 2A-B are schematic drawings showing side views of a portion of a patient being measured by, respectively, an impedance sensor and an optical sensor.
Figure 2B:
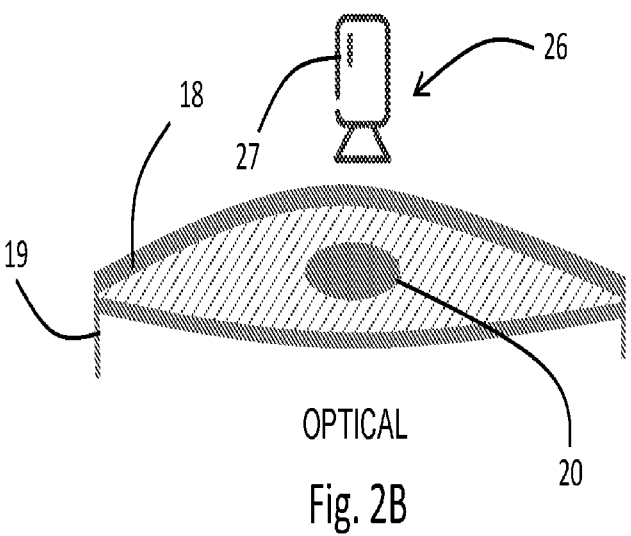

FIGS. 2A-B indicate how sensors 16, 26, incorporated in the system shown in FIG. 1 can measure signals that characterize time-dependent measurements of underlying tissue. Referring to FIG. 2A, an impedance sensor 16 features electrodes 17*a-d* that connect to a layer of skin 18 covering a portion of tissue 19 that includes a region of fluid build-up 20. The electrodes 17*a-d* connect to impedance circuitry (not shown in the figure) and sense signals that, once processed, determine the electrical impedance of tissue underneath them. More specifically, for the impedance measurement, the outer electrodes 17*a*, 17*d*, called 'drive electrodes,' inject a high-frequency (typically between 20-100 kHz), low-amperage (mean amplitude typically between 10-4000 μA) electrical current through the skin 18 and into the portion of tissue 19. Resistance of the surrounding tissue—which is affected by the fluid build-up 20—impacts current flow. It is manifested by a voltage drop measured by a pair of inner electrodes 17*b*, 17*c* called 'sense electrodes. This voltage drop is digitized by an analog-to-digital converter in the impedance system to yield a time-dependent impedance waveform. Analysis of changes in this waveform can indicate the resistance change and ultimately the degree of fluid-build-up 20 in the tissue portion 19.

Similarly, as shown in FIG. 2B, the system can also include an optical system 26, featuring an optical element 27 such as a camera (e.g., CCD camera) or combined light source, e.g., a light-emitting diode (herein "LED") or laser, and photodetector (e.g., photodiode) to detect swelling as described above. For example, swelling may manifest as a change in coloration of the skin 18. A camera can capture an image of the skin to detect this condition. In related embodiments, the combined light source and photodetector can measure the optical absorbance and/or reflectance of the skin and use these parameters to estimate the degree of swelling.

2. Clinical Results

Figures 3A, 3B, 3C:
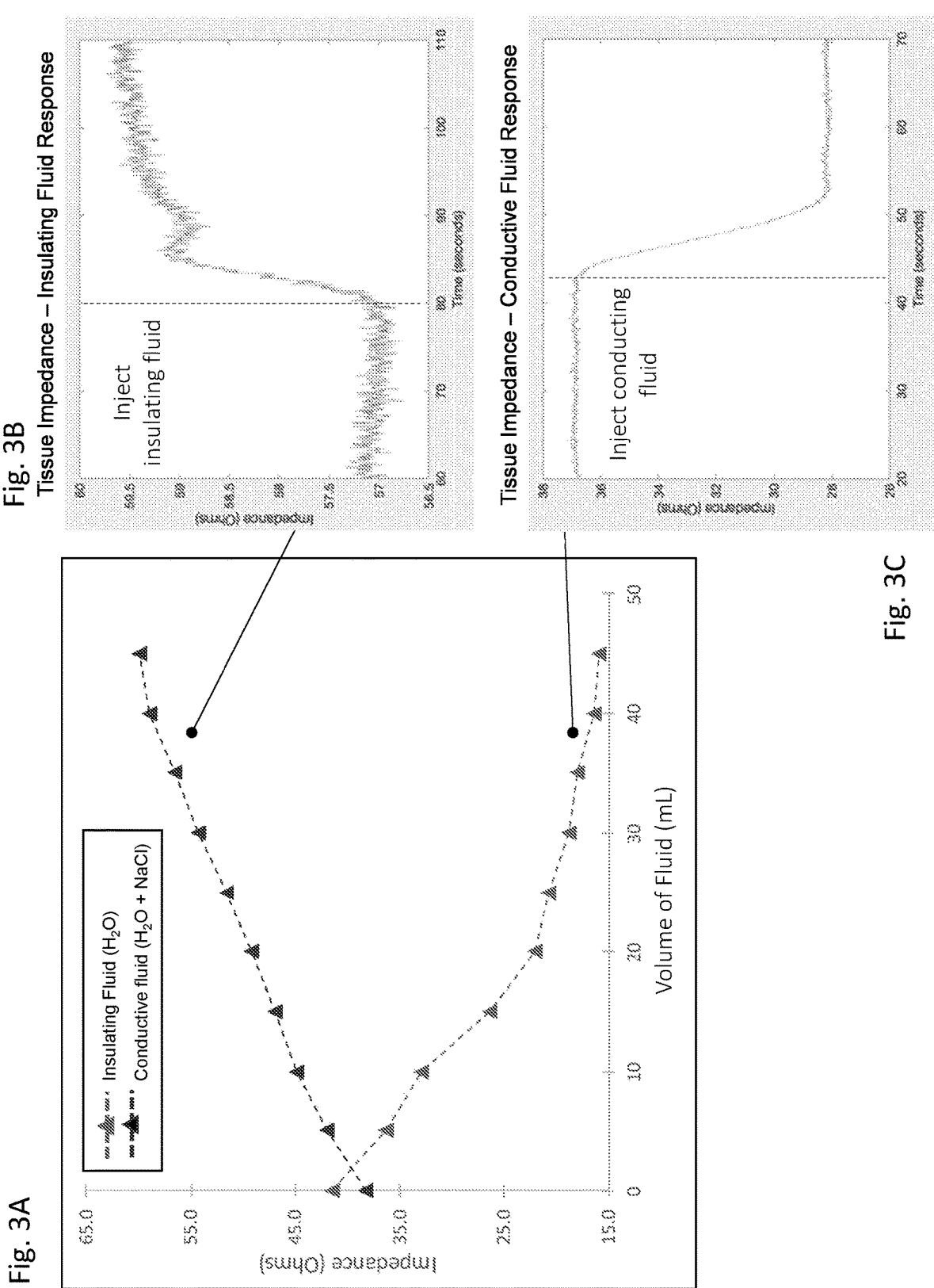
FIG. 3A is a graph showing changes in impedance measured as a function of fluid volume using an impedance sensor similar to that shown in FIG. 2A.
FIGS. 3B and 3C are graphs showing changes in impedance measured using an impedance sensor similar to that shown in FIG. 2A from, respectively, a sample containing an insulating fluid and a conducting fluid.

Referring to FIGS. 3A-C, swelling and electrical impedance's ability to measure it can be simulated with a benchtop rig. Here, a 'phantom' system was developed using a 3D-printed box filled with a mixture of agar (to provide a density similar to human tissue) and sponges (to absorb excess fluid). These components were covered with a layer of synthetic skin having electrical and mechanical properties matched to human skin (purchased from Syndaver Inc.; www.syndaver.com). An impedance sensor featuring two sense and two drive electrodes, similar to that shown in FIG. 2A, was then attached to the synthetic skin. The resultant system had a baseline impedance of about 37 Ohms. Once it was fully fabricated and the impedance sensor attached to its surface, a calibrated syringe was used to systematically inject both insulating (deionized water) and conductive (saline) solutions into the phantom. The impedance sensor then measured the resulting DC impedance signals.

As shown in FIG. 3A, as insulating deionized water is injected into the phantom, its overall impedance as measured by the impedance sensor systematically decreases. Likewise, injecting conducting saline into the phantom gradually increases the impedance. FIGS. 3B and 3C show, respectively, the time-dependent increase and decrease in the impedance signal, as measured by the impedance sensor. Dashed lines in each figure indicate when a small bolus (2 ml) of fluid is injected into the phantom. As indicated by the rapid change in DC signal level, the response time of the sensor to injected fluids is on the order of a few minutes; this is significantly faster than times scales associated with conditions such as lymphedema, which typically manifests over months.

Figure 4B:
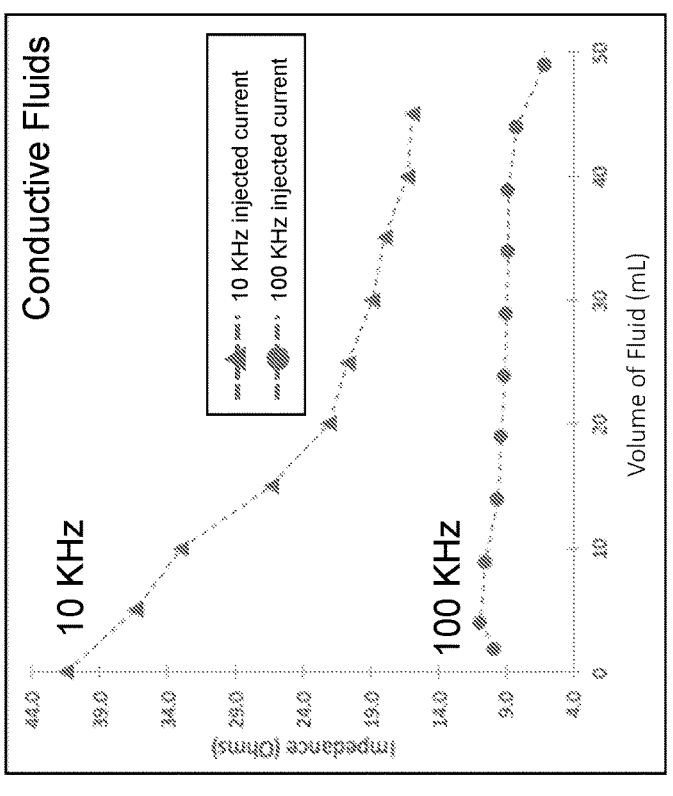
FIGS. 4A and 4B are graphs showing changes in impedance, measured at different frequencies of injected current, as a function of fluid volume using an impedance sensor similar to that shown in FIG. 2A from, respectively, a sample containing an insulating fluid and a conducting fluid.
Figure 4C:
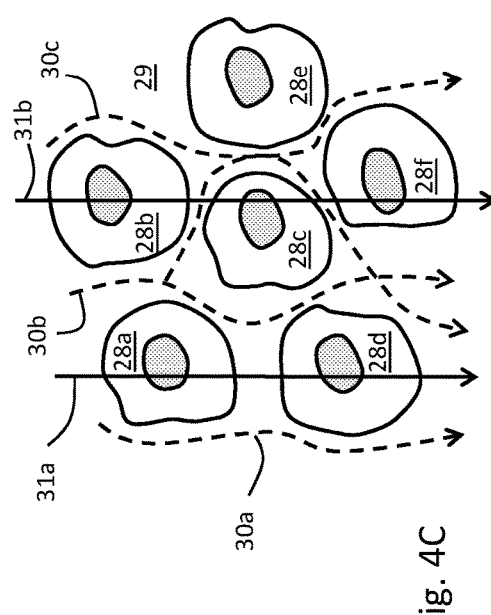
FIG. 4C is a schematic drawing of relatively high and low-frequency currents injected during an impedance measurement that pass, respectively, through cells and around cells in human tissue.
Figure 4A:
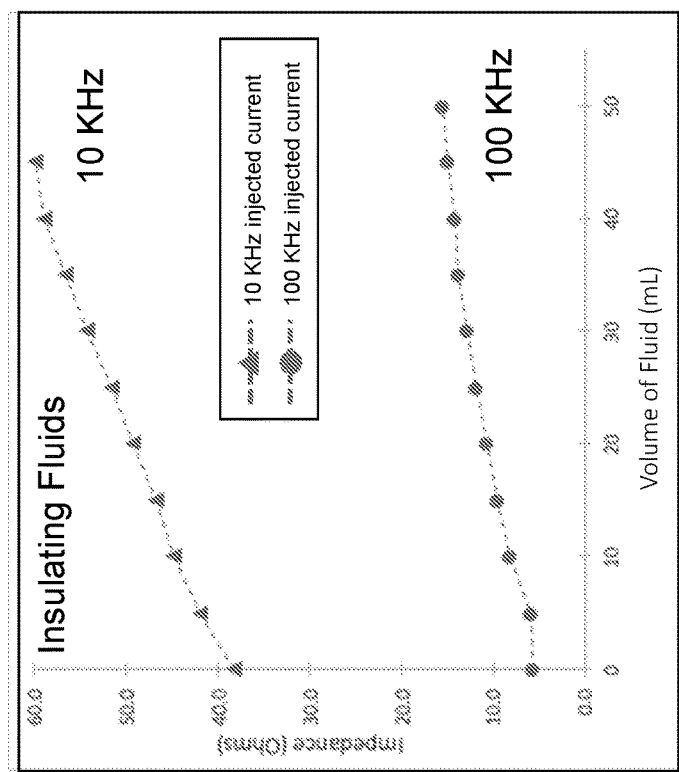

Referring to FIGS. 4A-C, the same phantom and impedance system used to generate data for FIGS. 3A-C was used to estimate the impact of the frequency of the injected current on signal magnitude. Here, using the same approach as described above, the frequency of the injected current was toggled between 10-100 KHz for both insulating deionized water (FIG. 4A) and conductive saline (FIG. 4B). As is clear from these figures, the change in impedance with a volume of injected fluid is more pronounced when measured at relatively low frequencies (e.g., 10 KHz) than higher frequencies (100 KHz). FIG. 4C shows a graphical representation of this phenomena that includes a series of cells 28*a-f* immersed in a fluid medium 29. Both the cells 28*a-f* and fluid medium 29 impact the impedance measurement made by the impedance sensor, as indicated in FIGS. 3A-C and 4A-B. However, as indicated by dashed lines 30*a-c*, relatively low frequencies of injected current pass around the cells 28*a-f*. Here, the capacitance of the cells' membranes prohibits current from passing through them. This indicates relatively low frequencies of injected current are likely to sample—and thus be more sensitive to—the extra-cellular fluids. These are likely the fluids that induce swelling (e.g. during lymphedema). In contrast, the low-frequency measurement should be less sensitive to the intracellular fluid, as this current does not pass through the cells 28*a-f*. Conversely, relatively high frequencies of injected current 31*a-b* can overcome the inherent capacitance of a typical cell membrane, as pass through both the cells 28*a-f* and fluid medium 29. Since both, these components contribute to the impedance signal, but only the extra-cellular fluids are increased by swelling, the relatively high-frequency current is less sensitive to a swelling-induced signal change.

3. Mechanical and Electrical Components

Figures 5A, 5B, 5C:
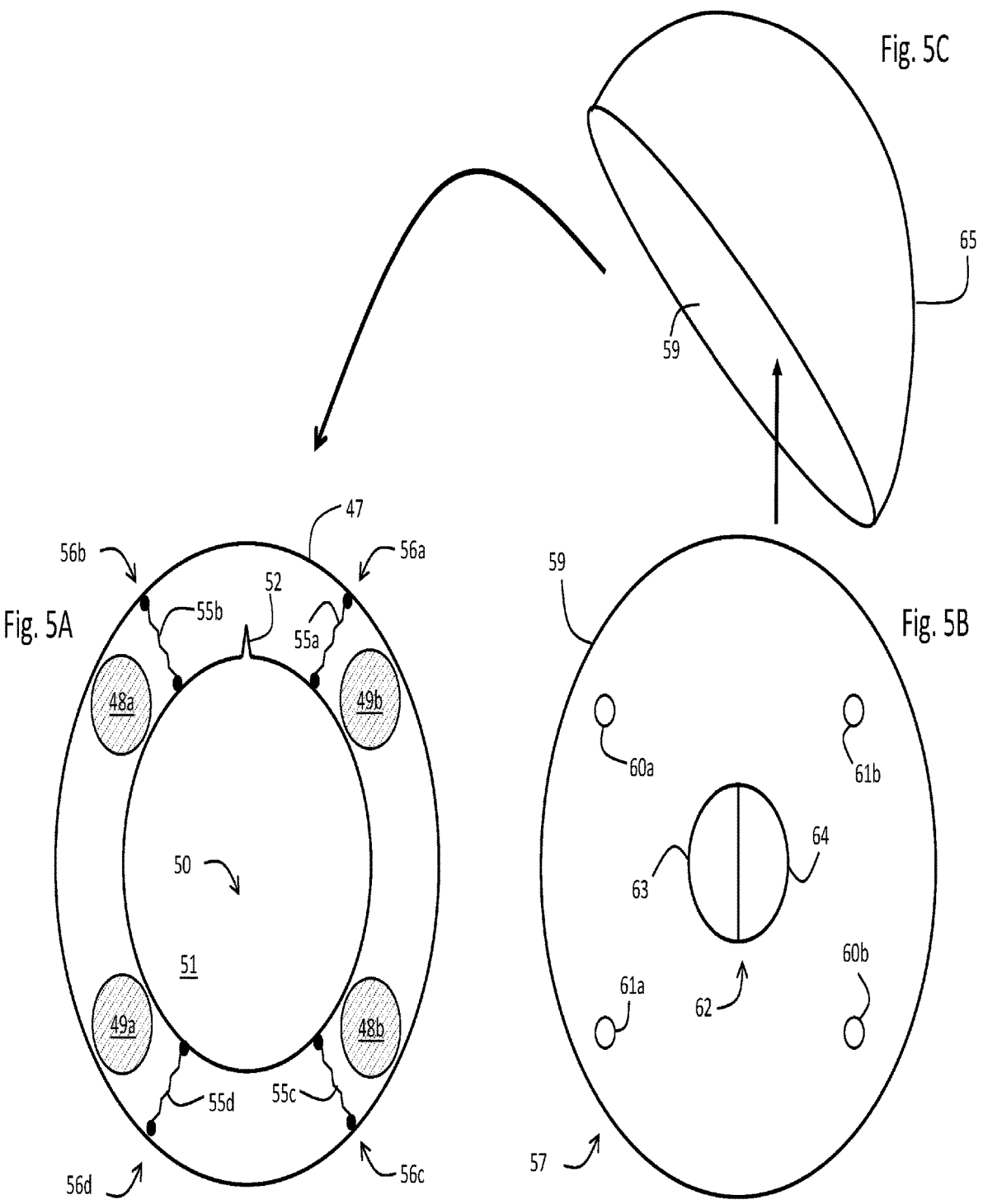
FIG. 5A is a schematic drawing of an electrode patch used in an embodiment of the invention.
FIG. 5B is a schematic drawing of a bottom surface of a circuit board used in a device that connects to the electrode patch shown in FIG. 8A during measurement of a patient.
FIG. 5C is a schematic drawing of an enclosure that encloses the circuit board of FIG. 5B.

FIGS. 5A-C shows another embodiment of the invention featuring a single electrode patch 47 that includes four distinct electrodes: sense electrodes 48*a*, 48*b* and drive electrodes 49*a*, 49*b*. The electrode patch 47 is shaped as an annular ring with an opening 50 in its center; through the opening 50, an optical system 62 (which, for example, can include one or more light sources, one or more photodetectors, and/or a more sophisticated imaging system such as a camera; not shown in the figure) can image a patient's skin 51, as described in more detail below. The annular ring's bottom surface supports both the sense 48a, 48b and drive 49a, 49b electrodes surrounding the opening 50. In an embodiment, electrode patch 47 features an alignment feature, which, as shown in FIG. 5A, is a notch 52 cut into the annular ring. For example, notch 52 may align with a corresponding alignment feature that is part of a marking on the patient (e.g. an anatomical feature on a patient's skin 51). Here, alignment with marking on a patient allows for repeatable positioning of the patch 47 at the same location every time, as described in more detail below.

As shown in FIG. 5A, and similar to the embodiments described herein, the electrode patch 47 features strain gauges 55a-d, which in this case are metal traces patterned in a serpentine manner across the width of the annular ring. The resistance of the metal traces changes as they are strained. Each strain gauge—which effectively forms a variable resistor—connects to a conventional circuit, such as a Wheatstone Bridge, that generates a measurable voltage impacted by the strain gauges' variable resistance. To accommodate strain, the electrode patch 47 is typically composed of a stretchable material, similar, for example, to Tegaderm® manufactured by 3M. The metal traces in the strain gauges 55a-d are terminated on each end with a pair of electrical contacts 56a-d; these are oriented to mate (i.e., come in electrical contact) with matched electrical contacts 58a-d patterned on a bottom surface 59 of a circular, battery-powered circuit board that forms the primary component of a device 65. When they touch, the electrical contacts 58a-d, 56a-d connect the strain gauges 55a-d (i.e., variable resistors) to individual Wheatstone Bridge circuits within the circuit board. Additionally, circuit board features the first set of electrical contacts 60a, 60b for the sense electrodes 48a,b, and a second set of electrical contacts 61a,b for the drive electrodes 49a, 49b. The electrical contacts 60a, 60b, 61a, 61b are typically thin metal films that, during use, electrically connect to a conductive rivet (not shown in the figure) inserted into hydrogel electrodes 48a, 48b, 49a, 49b. During a measurement, the contacts 61a, 61b transmit alternating current (herein "AC") into the patient's skin through the drive electrodes 49a, 49b while the contacts 60a, 60b port corresponding bioelectric signals to ECG and impedance circuits on the circuit board.

In embodiments, the electrode patch 47 can perform a 'complex' bioimpedance measurement, which is typically modeled by a mathematical equation featuring both real and imaginary components. Such a mathematical equation ultimately determines the time-dependent resistance and capacitance at the area of measurement. Further analyses of these parameters indicate additional physiological parameters.

For impedance measurements, the corresponding circuit typically injects alternating AC into the skin, wherein the frequency of the current typically varies from about 5 KHz to 500 KHz; in some embodiments, the circuit rapidly 'sweeps' the AC frequencies between these ranges. Technically, the impedance measured with the circuit is a complex term, wherein electrical resistance encountered by the electrical current represents the real component of the impedance, and reactance encountered by the current represents the imaginary component of the impedance. More specifically to this particular measurement, impedance (the real component of the signal) is typically impacted by the volume of fluid, whereas reactance (the imaginary component of the signal) is typically impacted by the electrostatic storage of charge (i.e., capacitance) caused by the fluid.

Namely, with reference to FIGS. 5A-C, in embodiments, during a measurement, the drive electrodes 49a, 49b inject a high-frequency, low-amperage current into the vessel. In embodiments, current injected from one drive electrode 49a is typically out of phase, for example 90° out of phase, with current injected from the opposing drive electrode 49b. In embodiments, the circuit board within the electronics unit comprises an impedance circuit that sequentially performs measurements of resistance (the "real" component of bioimpedance) and reactance (the "imaginary" component of bioimpedance).

In embodiments, the impedance circuit comprises a collection of discrete electrical components, such as operational amplifiers, resistors, and capacitors. In further embodiments the impedance circuit is integrated into a single small-scale semiconductor analog front end or 'chip', such as the MAX30009 manufactured by Maxim Semiconductor (Sunnyvale, CA). A battery typically powers the circuit board, for example a rechargeable lithium-ion battery.

As shown in Eq. 1 below, the impedance of a system is typically represented by as a complex quantity 'Z', with the polar form of Z including both its magnitude and phase characteristics:

$$Z = |Z| e^{i arg(Z)} \tag{1}$$

where the magnitude |Z| represents the ratio of the voltage amplitude to the current amplitude, and the argument arg(Z) is the phase difference between the voltage and current. Eq. 1 can be represented in Cartesian form as:

$$Z = R + iX \tag{2}$$

where the real part of the impedance is the resistance R and the imaginary part is the reactance X.

In an embodiment, after a measurement is made, the patch wirelessly transmits information (typically via Bluetooth) to an external gateway for further analysis.

Importantly, the MAX30009 can easily measure Z at multiple frequencies of injected current, typically ranging from 5-500 KHz. This combination of multi-frequency measurement of R and X allows determination of a host of electrical properties from the underlying tissue. Typically these are measured in the form of time-domain waveforms. Analysis of these waveforms with beat picking and machine-learning algorithms yields multiple physiological parameters, e.g. stroke volume, cardiac output, intra/extra-cellular fluids, and the like. Additionally, the patch can include small-scale electrical and optical measurement systems to determine conventional vital signs such as heart rate, respiratory rate, SpO$_2$, tissue perfusion via NIRS.

The body-worn patch 47 is a sophisticated physiological monitor that makes robust measurements of both hemodynamic parameters and vital signs, all within a small-scale, low-cost wearable package. Such a system could be used in the hospital, and accompany the patient as they transition to the home. In the hospital, the patch could easily integrate with other equipment, such as infusion pumps, peritoneal and hemodialysis equipment, hospital beds, vital signs monitors, and the like.

Figure 6A:
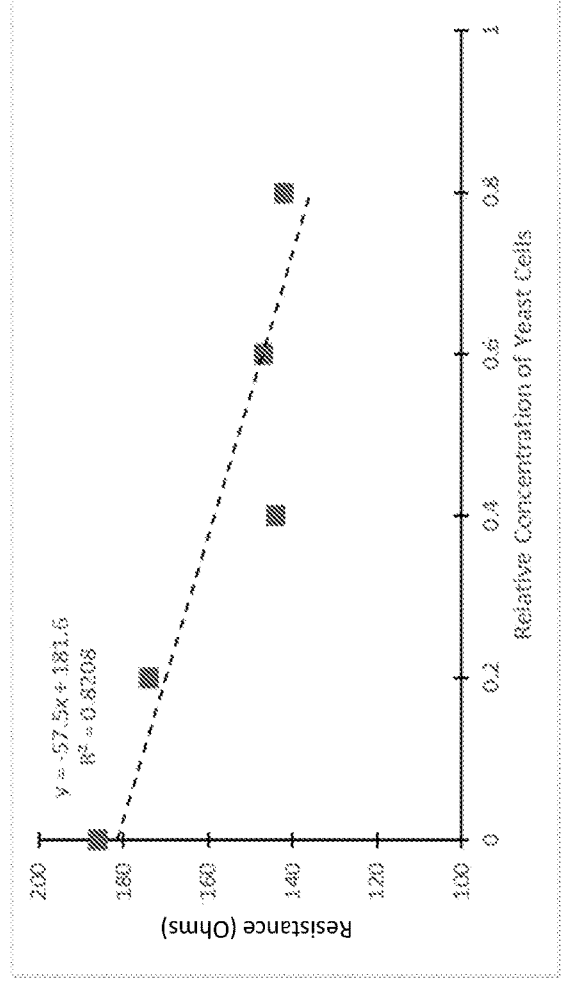
FIGS. 6A and 6B are graphs showing changes in impedance and resonant frequency associated with capacitance, respectively, as measured in an experimental test.
Figure 6B:
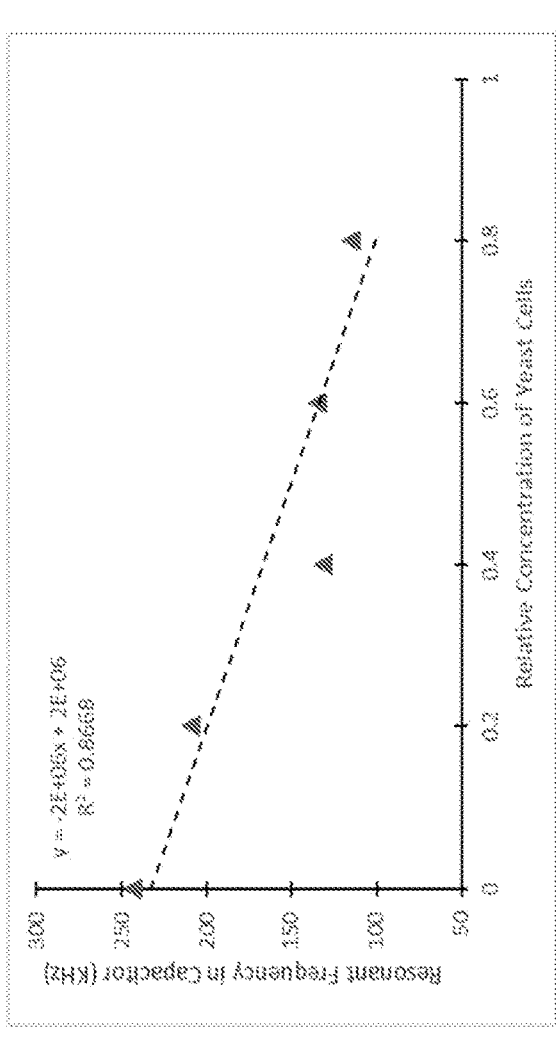

FIGS. 6A and 6B are graphs showing, respectively, changes in resistance and resonant frequency as measured in an experimental test with the body-worn patch 47 from a sample containing concentrations of yeast cells that were systematically varied. Yeast cells were used for this test because they are living cells and thus somewhat representative of human tissue, and also because their concentration could be easily varied during the test. Here, concentration-dependent resistance shown in FIG. 6A was determined from the real component of the impedance measurement, as described above. The concentration-dependent resonant frequency is the frequency at which the series inductance of the capacitor formed by the yeast cells is equal but opposite to its capacitance. In an actual measurement with a region of tissue, the resonant frequency therein will depend strongly on the composition of these tissue, including the presence of blood flow and underlying fluids (e.g. those accumulated during lymphedema). Thus detecting the resonant frequency, which is typically done using conventional beat-picking algorithms, during multi-frequency measurements may indicate these parameters.

Figures 7A, 7B:
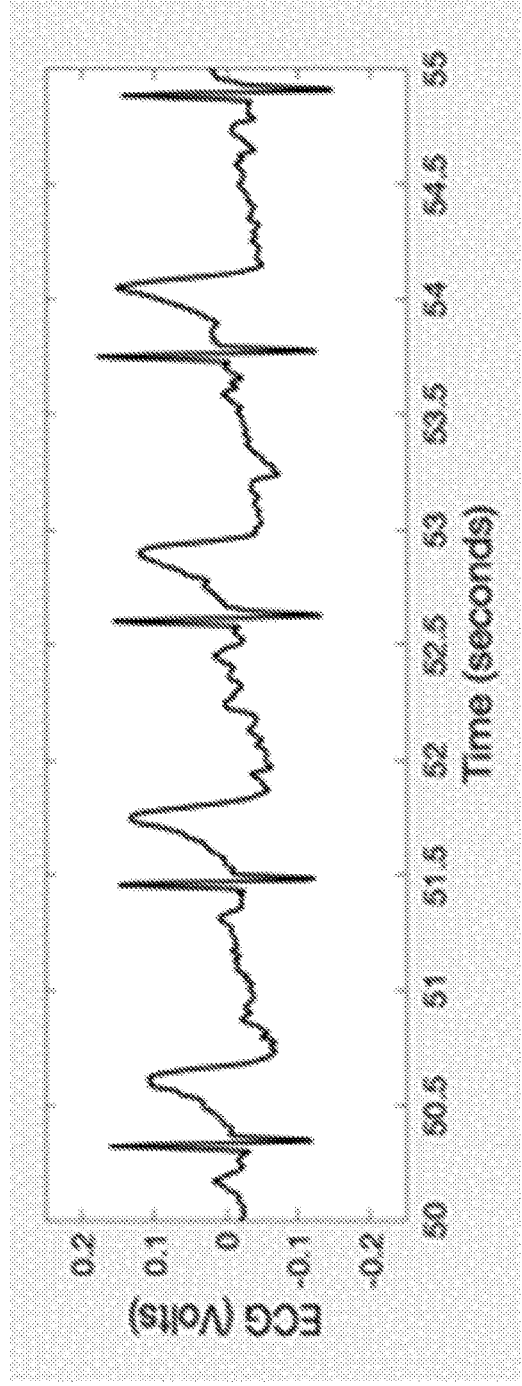
FIGS. 7A and 7B are graphs of time-dependent waveforms featuring heartbeat-induced pulses measured from a patient's chest using, respectively, an ECG sensor and an impedance sensor within the system of FIG. 1.

FIGS. 7A and 7B are graphs of time-dependent waveforms featuring heartbeat-induced pulses measured from a patient's chest using, respectively, an ECG sensor and an impedance sensor within body-worn patch 47. Such waveforms, for example, can be analyzed with algorithms to determine parameters such as heart rate, heart rate variability, respiration rate, stroke volume, and cardiac output. Examples of such algorithms are provided in the following issued patents, the contents of which are incorporated herein by reference: U.S. Pat. No. 11,141,072, entitled Necklace-shaped Physiological Sensor; U.S. Pat. No. 11,129,537, entitled Body-worn Sensor for Characterizing Patients with Heart Failure; U.S. Pat. No. 11,123,020, entitled Neck-worn Physiological Monitor; and U.S. Pat. No. 11,116,410, entitled Patch-based Physiological Sensor.

Figures 8A, 8B, 8C, 8D, 8E:
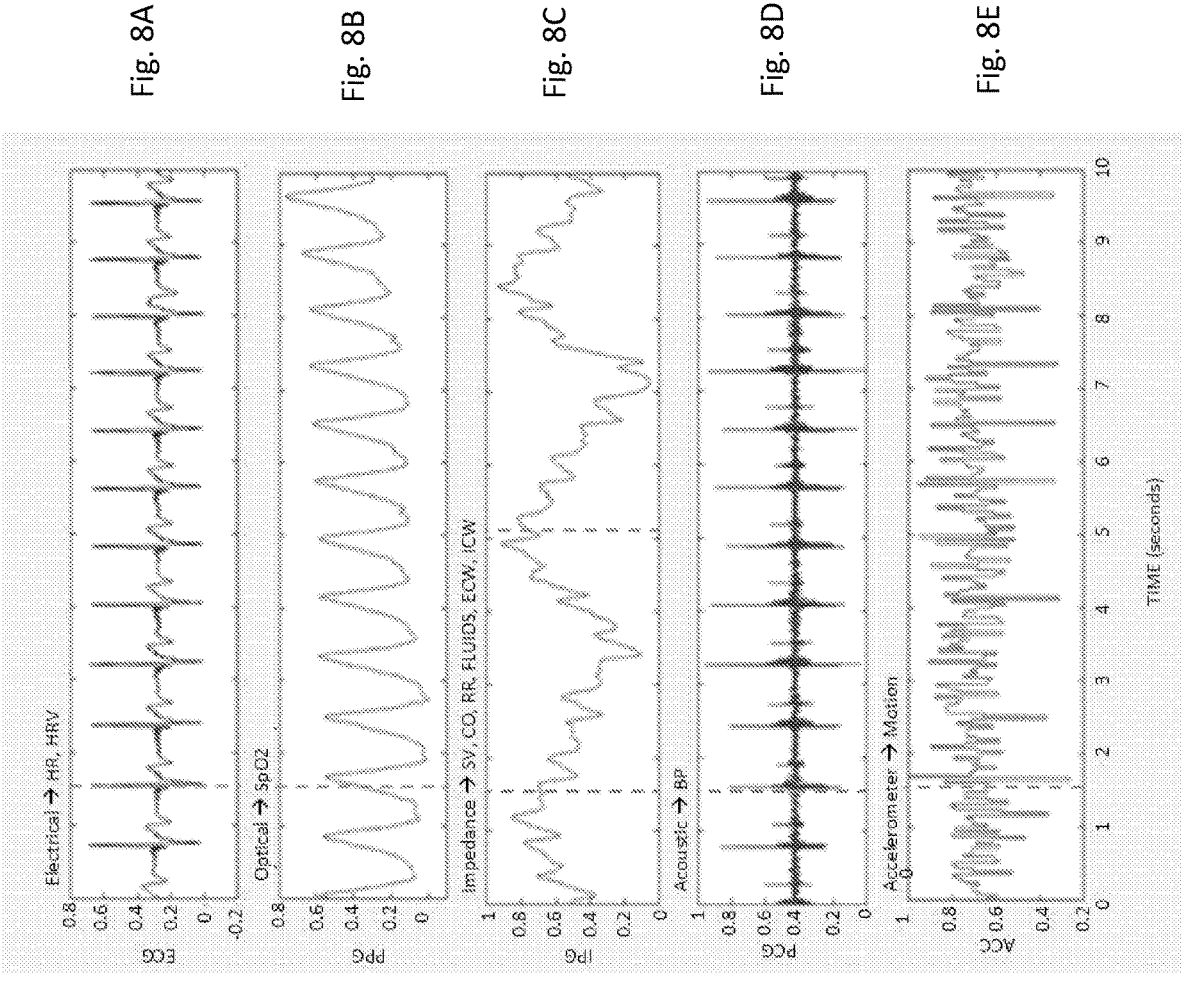
FIGS. 8A to 8E are graphs of time dependent waveforms of various physiological parameters measured from a patient's chest using the system of FIG. 1.
Figures 9A, 9B, 9C, 9D, 9E, 9F:
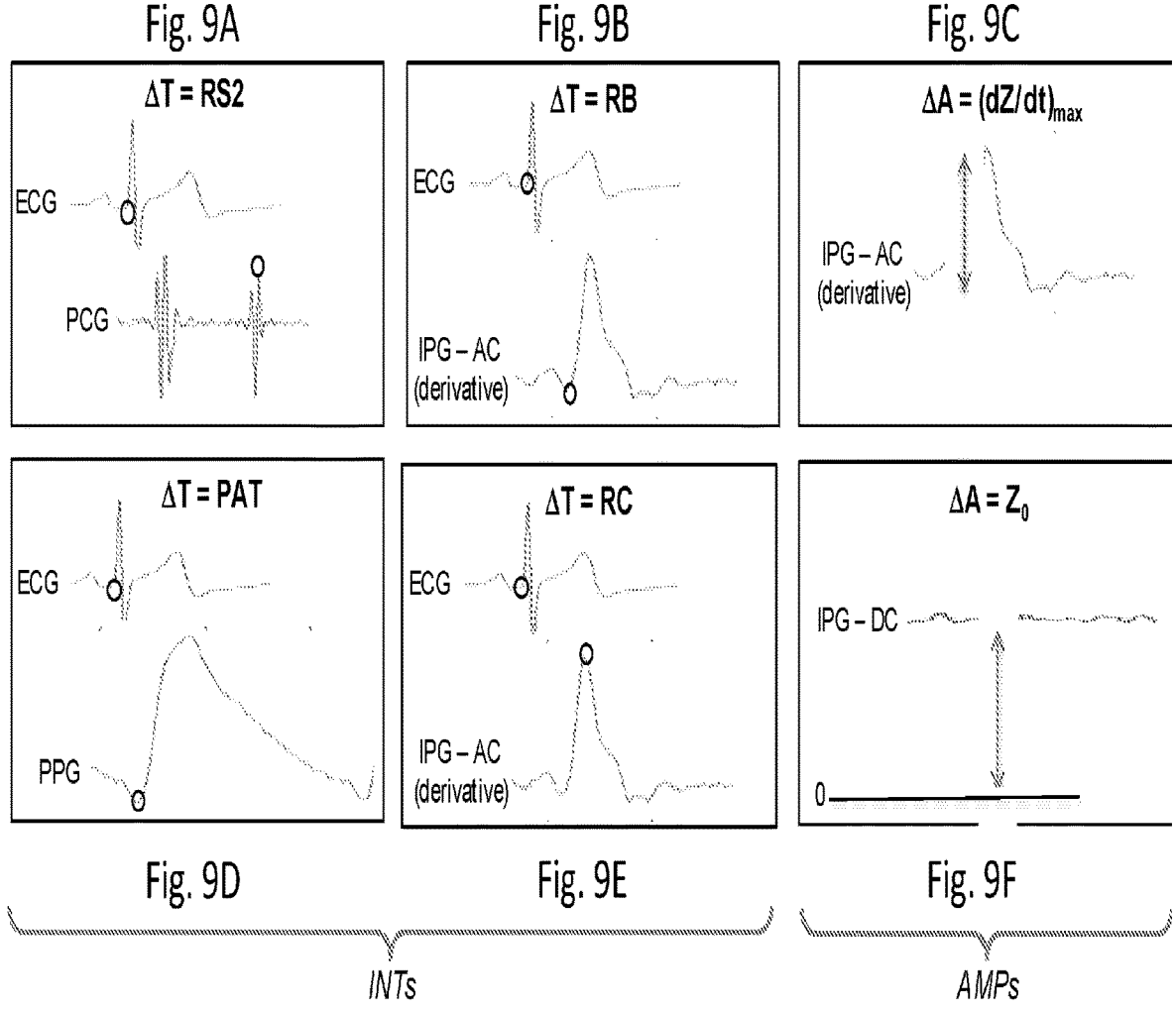
FIGS. 9A to 9F are graphs illustrating time-dependent fiducials determined from waveforms and amplitudes of heartbeat-induced pulses, and how these fiducials and pulses relate to blood pressure.

An ECG waveform measured by the patch sensor 47 is shown in FIG. 8A. It includes a heartbeat-induced QRS complex that informally marks the beginning of each cardiac cycle. FIG. 8D shows a phonocardiogram (PCG) waveform, which is measured with the acoustic module that can be incorporated in the body-worn patch and features the S1 and S2 heart sounds. FIG. 8B shows a photoplethysmogram (PPG) waveform, which is measured by the optical sensor, and indicates volumetric changes in underlying capillaries caused by heartbeat-induced blood flow. An impedance (IPG) waveform includes both DC ($Z_0$) and AC ($dZ(t)$) components: $Z_0$ indicates the amount of fluid in the tissue by measuring underlying complex electrical impedance as described aboce, and represents the baseline of the IPG waveform; $dZ(t)$, which is shown in FIG. 8C, tracks blood flow in the underlying vasculature and represents the pulsatile components of the IPG waveform. The time-dependent derivative of $dZ(t)$–$dZ(t)/dt$—includes a well-defined peak that indicates the maximum rate of blood flow in the thoracic vasculature. A motion waveform (ACC) measured by an accelerometer is shown in FIG. 8E.

Each pulse in the ECG waveform (FIG. 8A) features a QRS complex that delineates a single heartbeat. Feature-detection algorithms (e.g. beatpicking algorithms) operating in firmware on the patch sensor calculate time intervals between the QRS complex and fiducial markers on each of the other waveforms. For example, the time separating a 'foot' of a pulse in the PPG waveform (FIG. 8B) and the QRS complex is referred to as pulse arrival time (PAT). PAT relates to blood pressure (BP) and systemic vascular resistance. During a measurement, the patch sensor calculates PAT and vascular transit time (VTT) which is a time difference between fiducial markers in waveforms other than ECG, e.g. the S1 or S2 points in a pulse in the PCG waveform (FIG. 8D) and the foot of the PPG waveform (FIG. 8B). Or the peak of a pulse in the $dZ(t)/dt$ waveform and the foot of the PPG waveform (FIG. 8B). In general, any set of time-dependent fiducials determined from waveforms other than ECG can be used to determine VTT. Collectively, PAT, VTT, and other time-dependent parameters extracted from pulses in the four physiologic waveforms are referred to herein as 'INT' values. Additionally, firmware in the patch sensor calculates information about the amplitudes of heartbeat-induced pulses in some of the waveforms; these are referred to herein as 'AMP' values. For example, the amplitude of the pulse in the derivative of the AC component of the IPG waveform (($dZ(t)/dt$)max) indicates the volumetric expansion and forward blood flow of the thoracic arteries, and is related to systolic blood pressure (SYS) and the contractility of the heart.

The general model for calculating SYS, diastolic (DIA), and mean (MAP) blood pressures involves extracting a collection of NT and AMP values from the four physiologic waveforms measured by the patch sensor, and then using algorithms based in machine learning and artificial intelligence to process these values to determine blood pressure. FIGS. 9A-F, for example, show different INT and AMP values that may correlate to BP. NT values include the time separating R and S2 from a pulse in the PCG waveform (RS2, shown in FIG. 9A); the time separating R and the base of a derivative of a pulse from the AC component of the IPG waveform, referred to as point B (RB, FIG. 9B); the time separating R and the foot of a pulse in the PPG waveform (PAT, FIG. 9D); and the time separating R and the maximum of a derivative of a pulse from the AC component of the IPG waveform, referred to as point C (RC, FIG. 9E). AMP values include the maximum value of a derivative of a pulse from the AC component of the IPG waveform (($dZ(t)/dt$)max, FIG. 9C); and the maximum value of the DC component of the IPG waveform (Z0, FIG. 9F). Any of these parameters may be used, in combination with a calibration defined below, to determine blood pressure. All of these fiducial values can serve as input into the blood pressure model based on machine learning and artificial intelligence.

The method for determining BP according to the invention involves first calibrating the BP measurement during a short initial period, and then using the resulting calibration for subsequent measurements. The calibration process typically lasts for about 5 days. It involves measuring the patient multiple (e.g. 2-4) times with a cuff-based BP monitor employing oscillometry, while simultaneously collecting the INT and AMP values like those shown in FIGS. 9A-F. Each cuff-based measurement results in separate values of SYS, DIA, and MAP. In embodiments, one of the cuff-based BP measurements is coincident with a 'challenge event' that alters the patient's BP, e.g. squeezing a handgrip, changing posture, or raising their legs. The challenge events typically impart variation in the calibration measurements; this can help improve the ability of the calibration to track BP swings. Typically, the patch sensor and cuff-based BP monitor are in wireless communication with each other; this allows the calibration process to be fully automated, e.g. information between the two systems can be automatically shared without any user input. Processing the INT and AMP values, e.g. using the method shown in FIG. 9 and described in more detail below, results in a 'BP calibration'. This includes initial values of SYS and DIA, which are typically averaged from the multiple measurements made with the cuff-based BP monitor, along with a patient-specific model that is used in combination with selected INT and AMP values to cufflessly determine the patient's blood pressure. The calibration period (about 5 days), is consistent with a conventional hospital stay; after this, the patch sensor typically requires a new calibration to ensure accurate BP measurements.

On a more practical level, the above-described circuits process the bioelectric signals (e.g., filter and amplify them) to generate, respectively, analog time-dependent ECG, bio-impedance, and bio-reactance waveforms. These are then digitized with an analog-to-digital converter to yield digital waveforms suitable for follow-on processing. A micropro-cessor operating on the circuit board runs computer code that uses algorithms to process these types of waveforms, extract any fiducial features (e.g., signal levels of the imped-ance and reactance waveforms, QRS complexes from the ECG waveforms), and then processes these to estimate various physiological conditions (e.g. variable of RR inter-vals extracted from the QRS complexes) in the patient that might indicate other disease states (e.g. arrhythmias).

Referring again to FIGS. 5A-C, in other embodiments the circuit board can includes an optical sensor 62 that, in turn, features a light source 63 and a photodetector 64 operating in a reflection-mode geometry to determine optical proper-ties (e.g., coloration, texture) of the patient's skin 51. During use, the light source 63 irradiates a region of the patient's skin 51. Radiation reflecting off the region will be impacted by conditions such as redness and mottling of the skin 51; the photodetector 64 senses the reflected radiation and generates a signal, which is then filtered and amplified by the corresponding circuitry on the circuit board. An algorithm then analyzes the optical signal to estimate changes in the skin coloration that may, for example, indicate the progres-sion of lymphedema. In embodiments, the light source 63 may be a collection or array of light sources (typically light-emitting diodes or laser diodes), each emitting radia-tion at a different wavelength. Alternatively, the light source 63 may be a 'white' light source (e.g., a multi-wavelength LED or tungsten lamp) that emits a collection of wave-lengths throughout the visible, infrared and ultraviolet spec-tra. The photodetector 64 is typically a single photodiode or an array of photodiodes. Alternatively, it can be an imaging system (e.g., a CCD camera) configured to collect a spatial image of the underlying skin.

During use, the electrode patch 47 is applied to the patient's skin 51 so that the opening 50, the annular ring, and the patch's alignment feature 52 are aligned with an align-ment feature on the patient. If swelling is present, it may be necessary to stretch the patch 47 so that the sensing location is entirely visible. This stretching, as described above, will induce strain in the strain gauges 55*a-d*. The device 65 featuring the above-described sensors then snaps into the electrode patch 47 so that electrical contacts 60*a,b* and 61*a,b* in electrical contact with an internal impedance circuit align with the different sets of sense 48*a,b* and drive 49*a,b* electrodes, and electrical contacts 58*a-d* align with the contacts 56*a-d* associated with the strain gauges. Note that all electrical contacts must be large enough to accommodate any stretching of the patch 47. With this process, the electrode patch 47 is consistently placed in the same loca-tion, allowing repeatable measurements to be made using various circuits within the circuit board, as described above.

Typically, the electrode patch is composed of a foam substrate with an adhesive layer on its bottom surface. The sense 48*a,b* and drive 49*a,b* electrodes are typically made from a hydrogel material that is typically adhesive, electri-cally conductive and features an electrical impedance matched to the patient's skin. Electrical traces and contacts are typically composed of conductive materials, such as metal films or conductive ink. Electrodes may also be dry electrodes made of metals (e.g., tin, silver, sintered Ag/AgCl, gold, platinum, and stainless steel) or polymers (e.g., EDPM rubber with additives).

In related embodiments, the positioning location can be imaged (e.g., by taking a photograph of it with a conven-tional mobile phone) to indicate the degree of lymphedema-induced swelling. For example, the physical deformation of the skin (e.g., stretching) may indicate the degree of swell-ing. During use, the patient may use their mobile phone and a customized software application to take a photo of the skin before the electrode patch is applied. The software applica-tion transmits the photograph to a cloud-based system, where image-processing algorithms (e.g., those using arti-ficial intelligence or machine learning) can evaluate it to estimate separation between features in the skin and, from this, the degree of swelling. Results from the image-pro-cessing algorithms and algorithms that process sensor-gen-erated waveforms may be combined to enhance the deter-mination of lymphedema. In other embodiments, the electrode patch can have other shapes, such as square, rectangular, oval, and the like.

In a related embodiment, circuits used in the above-described sensors can be temporarily printed on the patient's body using conductive ink or electroconductive paint. Such a circuit may interface with an onboard microelectronic chip and be configured with sensors such as a strain gauge to determine the expansion of the limb and electrodes to assess limb fluid content using bioimpedance.

These and other embodiments of the invention are deemed to be within the scope of the following claims.

What is claimed is:

1. A system for characterizing a patient, comprising:
   a substrate configured to be worn on a region of tissue of the patient;
   a first electrode and a second electrode disposed along an annular ring, wherein the first electrode and the second electrode are connected to the substrate and configured to be attached to the patient above the region of tissue;
   a plurality of strain gauges, each strain gauge comprising a metal trace patterned across a width of the annular ring; and
   an electrical system connected to the substrate and con-figured to be worn entirely on the patient's body, the electrical system in electrical contact with both the first and second electrodes and the plurality of strain gauges and configured to:
   (1) inject an alternating electrical current through the first electrode and into the region of tissue,
   (2) measure a first electrical signal from the region of tissue through the second electrode, wherein the first electrical signal indicates a resistance of the region of tissue,
   (3) measure a second electrical signal from the region of tissue through the second electrode, wherein the second electrical signal indicates a reactance of the region of tissue, and
   (4) determine swelling beneath a surface of the region of tissue based on the resistance and the reactance of the region of tissue and a signal from the plurality of strain gauges.

2. The system of claim 1, wherein the region of tissue is a chest of the patient.

3. The system of claim 1, wherein the resistance and the reactance are used to determine a bioimpedance measure-ment.

4. The system of claim 3, wherein the bioimpedance measurement is a complex bioimpedance measurement that includes a real component and an imaginary component.

5. The system of claim 4, wherein the real component is associated with the resistance and the imaginary component is associated with the reactance.

6. The system of claim 1, wherein the plurality of strain gauges includes four strain gauges.

7. The system of claim 6, wherein the four strain gauges are disposed concentrically around a center point of the region of tissue of the patient.

8. The system of claim 1, further comprising an optical system, configured to measure swelling on the region of tissue.

9. A system for characterizing a patient, comprising:

a substrate configured to be worn on a region of tissue of the patient;

a first electrode and a second electrode disposed along an annular ring, wherein the first electrode and the second electrode are connected to the substrate and configured to be attached to the patient above the region of tissue;

a plurality of strain gauges, each strain gauge comprising a metal trace patterned across a width of the annular ring; and an electrical system connected to the substrate and configured to be worn entirely on the patient's body, the electrical system in electrical contact with both the first and second electrodes and configured to:

(1) inject an alternating electrical current at a plurality of different frequencies through the first electrode and into the region of tissue, and (2) measure a set of electrical signals from the region of tissue through the second electrode, with each electrical signal in the set measured after injecting the alternating electrical current at a unique frequency into the region of tissue; and a processor in communication with the electrical system configured to receive the set of electrical signals, receive a signal from the strain gauge, process the set of electrical signals and the signal from the strain gauge, and determine swelling beneath a surface of the region of tissue.

10. The system of claim 9, wherein the region of tissue is a chest of the patient.

11. The system of claim 9, wherein the property is a bioimpedance measurement.

12. The system of claim 11, wherein a resistance and a reactance are used to determine the bioimpedance measurement.

13. The system of claim 12, wherein the bioimpedance measurement is a complex bioimpedance measurement that includes a real component and an imaginary component.

14. The system of claim 13, wherein the real component is associated with the resistance and the imaginary component is associated with the reactance.

15. The system of claim 9, wherein the plurality of strain gauges includes four strain gauges.

16. The system of claim 15, wherein the four strain gauges are disposed concentrically around a center point of the region of tissue of the patient.

17. The system of claim 9, further comprising an optical system, configured to measure swelling on the region of tissue.

18. The system of claim 17, wherein swelling is measured via time-dependent visual information captured by the optical system.

*  *  *  *  *